US011730418B2

(12) United States Patent
Kim

(10) Patent No.: US 11,730,418 B2
(45) Date of Patent: Aug. 22, 2023

(54) CARDIAC MONITORING SYSTEM WITH SUPRAVENTRICULAR TACHYCARDIA (SVT) CLASSIFICATIONS

(71) Applicant: West Affum Holdings Corp., Grand Cayman (KY)

(72) Inventor: Jaeho Kim, Redmond, WA (US)

(73) Assignee: West Affum Holdings DAC, Dublin (IE)

( * ) Notice: Subject to any disclaimer, the term of this patent is extended or adjusted under 35 U.S.C. 154(b) by 0 days.

(21) Appl. No.: 17/000,496

(22) Filed: Aug. 24, 2020

(65) Prior Publication Data
US 2021/0052181 A1 Feb. 25, 2021

Related U.S. Application Data

(60) Provisional application No. 62/891,216, filed on Aug. 23, 2019, provisional application No. 62/890,313, filed on Aug. 22, 2019.

(51) Int. Cl.
*A61B 5/361* (2021.01)
*A61B 5/363* (2021.01)
(Continued)

(52) U.S. Cl.
CPC .............. *A61B 5/366* (2021.01); *A61B 5/282* (2021.01); *A61B 5/35* (2021.01); *A61B 5/352* (2021.01);
(Continued)

(58) Field of Classification Search
CPC ........ A61N 1/395; A61N 1/3624; A61B 5/35; A61B 5/361; A61B 5/363; A61B 5/366; A61B 5/352
See application file for complete search history.

(56) References Cited

U.S. PATENT DOCUMENTS 3,724,355 A 4/1973 Busch et al.
3,724,455 A 4/1973 Unger
(Continued)

FOREIGN PATENT DOCUMENTS

WO 9839061 A2 9/1998

OTHER PUBLICATIONS

Heartstart MRx and XL AED Algorithm—Application Note, Jul. 2001, Edition 2 Philips Healthcare, USA.
(Continued)

*Primary Examiner* — George R Evanisko
(74) *Attorney, Agent, or Firm* — Spectrum IP Law Group LLC

(57) ABSTRACT

In one example, a cardiac monitoring system comprises a processor to receive a segment of an electrocardiogram (ECG) signal of a patient, and a memory to store the segment of the ECG. The processor is configured to identify QRS complexes in the segment of the ECG signal, generate a supraventricular (SV) template for SV complexes in the QRS complexes, identify SV complexes in the QRS complexes using the template, identify normal sinus rhythm (NSR) complexes in the segment of the ECG signal, obtain an atrial template for atrial waveforms in the NSR complexes, measure a range of a P-wave of the atrial waveforms from the NSR complexes, save the measured P-waves, and classify the identified SV complexes as either atrial fibrillation (AF) or supraventricular tachycardia (SVT) using the atrial template. Other examples and related methods are also disclosed herein.

6 Claims, 12 Drawing Sheets

(51) Int. Cl.
*A61B 5/366* (2021.01)
*A61N 1/39* (2006.01)
*A61B 5/35* (2021.01)
*A61B 5/282* (2021.01)
*A61B 5/352* (2021.01)

(52) U.S. Cl.
CPC .............. *A61B 5/361* (2021.01); *A61B 5/363* (2021.01); *A61N 1/395* (2013.01); *A61N 1/3956* (2013.01)

(56) References Cited

U.S. PATENT DOCUMENTS

| | | | |
|---|---|---|---|
| 4,583,524 A | 4/1986 | Hutchins | |
| 4,619,265 A | 10/1986 | Morgan et al. | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,348,008 A | 9/1994 | Bomn et al. | |
| 5,353,793 A | 10/1994 | Bomn | |
| RE34,800 E | 11/1994 | Hutchins | |
| 5,394,892 A | 3/1995 | Kenny et al. | |
| 5,405,362 A | 4/1995 | Kramer et al. | |
| 5,474,574 A | 12/1995 | Payne et al. | |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder et al. | |
| 6,427,083 B1 | 7/2002 | Owen et al. | |
| 6,529,875 B1 | 3/2003 | Nakajima et al. | |
| 6,546,285 B1 | 4/2003 | Owen et al. | |
| 6,597,943 B2 | 7/2003 | Taha et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,099,715 B2 | 8/2006 | Korzinov et al. | |
| 7,212,850 B2 | 5/2007 | Prystowsky et al. | |
| 7,559,902 B2 | 7/2009 | Ting et al. | |
| 7,587,237 B2 | 9/2009 | Korzinov et al. | |
| 7,865,238 B2 | 1/2011 | Brink | |
| 7,870,761 B2 | 1/2011 | Valentine et al. | |
| 7,907,996 B2 | 3/2011 | Prystowsky et al. | |
| 7,941,207 B2 | 5/2011 | Korzinov | |
| 7,974,689 B2 | 7/2011 | Volpe et al. | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,548,557 B2 | 10/2013 | Garstka et al. | |
| 8,615,295 B2 | 12/2013 | Savage et al. | |
| 8,644,925 B2 | 2/2014 | Volpe et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,089,685 B2 | 7/2015 | Sullivan et al. | |
| 9,131,901 B2 | 9/2015 | Volpe et al. | |
| 9,132,267 B2 | 9/2015 | Kaib | |
| 9,314,210 B2 | 4/2016 | Li | |
| 9,408,548 B2 | 8/2016 | Volpe et al. | |
| 9,454,219 B2 | 9/2016 | Volpe et al. | |
| 9,591,986 B2 | 3/2017 | Maskara et al. | |
| 9,592,403 B2 | 3/2017 | Sullivan | |
| 9,655,537 B2 | 5/2017 | Bardy et al. | |
| 9,826,911 B2 | 11/2017 | Fu et al. | |
| 9,907,477 B2 | 3/2018 | Quan et al. | |
| 9,955,887 B2 | 5/2018 | Hughes et al. | |
| 9,999,368 B2 | 6/2018 | Perschbacher et al. | |
| 10,016,143 B2 | 7/2018 | Siejko | |
| 10,039,469 B2 | 8/2018 | Higgins et al. | |
| 10,045,710 B2 | 8/2018 | Higgins et al. | |
| 2001/0056245 A1* | 12/2001 | Mlynash | A61B 5/35 600/513 |
| 2011/0022105 A9 | 1/2003 | Owen et al. | |
| 2003/0144700 A1* | 7/2003 | Brown | A61N 1/3622 600/518 |
| 2003/0158593 A1 | 8/2003 | Heilman et al. | |
| 2004/0059327 A1* | 3/2004 | Jenkins | A61B 18/1492 606/41 |
| 2004/0111120 A1* | 6/2004 | Sarkar | A61N 1/3956 607/5 |
| 2004/0243014 A1 | 12/2004 | Lee et al. | |
| 2005/0107833 A1 | 5/2005 | Freeman et al. | |
| 2005/0107834 A1 | 5/2005 | Freeman et al. | |
| 2006/0217621 A1 | 9/2006 | Kim et al. | |
| 2008/0312709 A1 | 12/2008 | Volpe et al. | |
| 2009/0005827 A1 | 1/2009 | Weintraub et al. | |
| 2009/0275849 A1 | 11/2009 | Stewart | |
| 2010/0007413 A1 | 1/2010 | Herleikson et al. | |
| 2010/0298899 A1 | 11/2010 | Donnelly et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0025131 A1 | 1/2014 | Sullivan et al. | |
| 2014/0070957 A1 | 3/2014 | Longinotti-Buitoni et al. | |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0328472 A1 | 11/2015 | Sullivan et al. | |
| 2016/0004831 A1 | 1/2016 | Carlson et al. | |
| 2016/0082277 A1 | 3/2016 | Foshee, Jr. et al. | |
| 2017/0296076 A1 | 10/2017 | Mahajan et al. | |
| 2019/0159733 A1 | 5/2019 | Shusterman | |
| 2019/0336026 A1 | 11/2019 | Dawoud et al. | |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

(56) References Cited

OTHER PUBLICATIONS

The LifeVest Network/Patient Data Management System, Zoll, 2015, 2000503 Rev A.

* cited by examiner

CARDIAC MONITORING SYSTEM WITH SUPRAVENTRICULAR TACHYCARDIA (SVT) CLASSIFICATIONS

CROSS-REFERENCE TO RELATED APPLICATIONS

The present application claims the benefit of U.S. Provisional Application No. 62/890,313 (C00003612.USP1) filed Aug. 22, 2019 and the benefit of U.S. Provisional Application No. 62/891,216 (C00003614.USP1) filed Aug. 23, 2019. Said Application No. 62/890,313 and said Application No. 62/891,216 are hereby incorporated herein by reference in their entireties.

BACKGROUND

Cardiac monitoring systems can continuously monitor a patient's electrocardiogram (ECG) signal to generate a rhythm classification. Because the ECG signals can be a mixture of multiple different QRS morphologies, using only heart rate (HR) and HR variability can produce incorrect heart rhythm classification, especially in classifying supraventricular tachycardia (SVT) rhythms. For example, atrial fibrillation (AF) and SVT rhythms can have high HR variability, so a cardiac monitoring system may have difficulty distinguishing between AF and SVT rhythms if only HR variability is used. A noisy ECG signal can increase the difficulty. Existing rhythm methods based on RR interval variability may have a high percentage of AF false positive alarms due to noise, PR interval variability, premature ventricular contractions (PVCs), and premature atrial contractions (PACs).

DESCRIPTION OF THE DRAWING FIGURES

Claimed subject matter is particularly pointed out and distinctly claimed in the concluding portion of the specification. However, such subject matter may be understood by reference to the following detailed description when read with the accompanying drawings in which:

Figure 1:
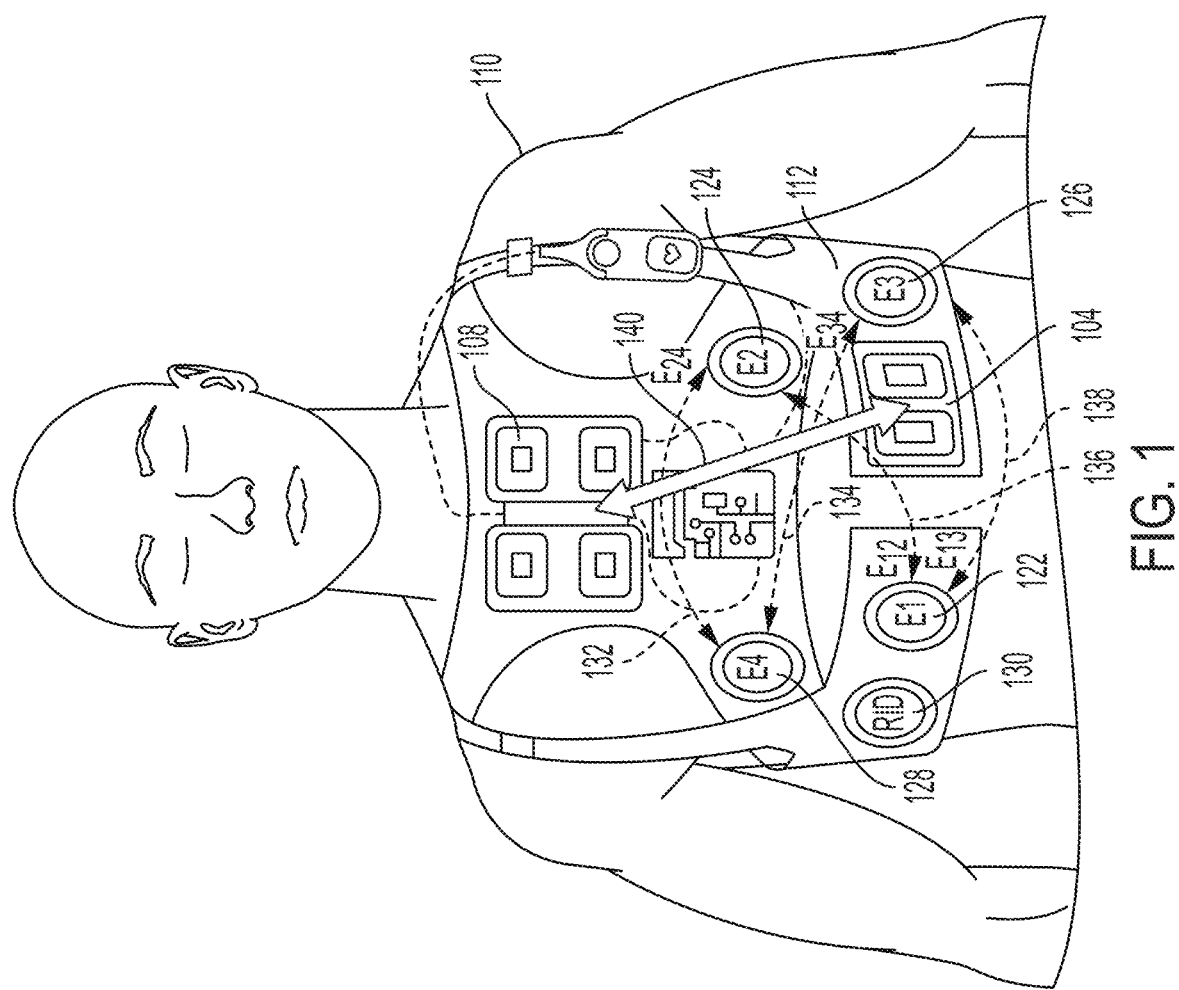
FIG. 1 is a diagram of four electrocardiograms (ECG) monitoring vectors used in an ECG monitoring device in accordance with one or more embodiments.

It will be appreciated that for simplicity and/or clarity of illustration, elements illustrated in the figures have not necessarily been drawn to scale. For example, the dimensions of some of the elements may be exaggerated relative to other elements for clarity. Further, if considered appropriate, reference numerals have been repeated among the figures to indicate corresponding and/or analogous elements.

DETAILED DESCRIPTION

In the following detailed description, numerous specific details are set forth to provide a thorough understanding of claimed subject matter. It will, however, be understood by those skilled in the art that claimed subject matter may be practiced without these specific details. In other instances, well-known methods, procedures, components and/or circuits have not been described in detail.

In the following description and/or claims, the terms coupled and/or connected, along with their derivatives, may be used. In particular embodiments, connected may be used to indicate that two or more elements are in direct physical and/or electrical contact with each other. Coupled may mean that two or more elements are in direct physical and/or electrical contact. However, coupled may also mean that two or more elements may not be in direct contact with each other, but yet may still cooperate and/or interact with each other. For example, "coupled" may mean that two or more elements do not contact each other but are indirectly joined together via another element or intermediate elements. Finally, the terms "on," "overlying," and "over" may be used in the following description and claims. "On," "overlying," and "over" may be used to indicate that two or more elements are in direct physical contact with each other. It should be noted, however, that "over" may also mean that two or more elements are not in direct contact with each other. For example, "over" may mean that one element is above another element but not contact each other and may have another element or elements in between the two elements. Furthermore, the term "and/or" may mean "and", it may mean "or", it may mean "exclusive-or", it may mean "one", it may mean "some, but not all", it may mean "neither", and/or it may mean "both", although the scope of claimed subject matter is not limited in this respect. In the following description and/or claims, the terms "comprise" and "include," along with their derivatives, may be used and are intended as synonyms for each other.

Referring now to FIG. 1 is a diagram of an electrocardiogram (ECG) monitoring device using four ECG monitoring vectors in accordance with one or more embodiments. A cardiac monitoring system or device can comprise a wearable cardioverter defibrillator (WCD) or a wearable cardiac monitor (WCM) that is configured to continuously monitor an electrocardiogram (ECG) signal of a patient 110 and generate a rhythm discrimination. FIG. 1 shows the relationship between physical electrode placement and ECG vector naming conventions. Electrodes E1, E2, E3, and E4 are the single-ended monitored electrodes and RLD is the Right Leg Drive electrode used to manage common mode noise.

In example shown in FIG. 1, a patient 110 can wear a support structure 112 that may comprise a wearable garment or vest or the like. In some examples, support structure 112 can include four ECG electrodes comprising electrode 122 (E1), electrode 124 (E2), electrode 126 (E3), and electrode 128 (E4). In addition, support structure 112 can include a common mode electrode 130 referred to as a right leg drive (RLD) electrode. The electrodes can couple with the ECG monitoring device such as a WCD or a WCM to obtain the ECG signals of the patient 110. The ECG signals can be digitized by the cardiac monitoring device for digital processing.

In some examples, differential vectors can be formed by subtracting two digitized ECG signals. ECG rhythm analysis then can be performed on these four vectors. Vectors E12, E13, E34, and E24 are the differential vectors that are derived from the single-ended vectors. Such differential vectors may include, for example, vector (E24) 132, vector (E34) 134, vector (E12) 136, and vector (E13) 138. The defibrillator shock vector 140 may be generated between the anterior defibrillation pad 104 and the posterior defibrillation pad 108. The ECG analysis algorithm includes provisions for excluding vectors that have noise or when a leads-off condition or situation is detected. Monitoring four vectors rather than monitoring two vectors is believed to contribute to enhanced ECG signal analysis and processing of the shock application algorithm to reduce the number of false shock events.

In one or more embodiments, the signals from four ECG electrodes can be combined to form six different vectors. In some embodiments, an ECG monitoring device can use four vectors for QRS complex analysis or heart rate analysis to determine if a shock should be applied. In some examples, a WCD device can be capable of performing the analysis and shock application determination if one or more of the vectors is noisy or one or more of the ECG leads is in a lead-off condition wherein the lead is not contacting the patient's skin or is not sufficiently contacting the patient's skin to allow an ECG signal to be obtained with that ECG lead. In some embodiments, three ECG electrodes may be used and three ECG vectors may be analyzed. In other embodiments, five or six ECG vectors may be analyzed using four ECG electrodes. In some embodiments, a single vector is used and analyzed. It should be noted that in general an ECG monitoring device can use and analyze fewer than four vectors or greater than four vectors, and the number of vectors can be increased beyond six vectors by using additional ECG electrodes, and the scope of the disclosed subject matter is not limited in this respect. In some examples, an ECG monitoring device can use four channels out of six possible differential channels formed from four independent electrodes placed around the chest of a patient 110. In other embodiments, a different number of channels, including only one channel, can be used. In embodiments where the ECG monitoring device comprises a WCM, a different number of electrodes can be used, often a reduced number of electrodes, or a different garment system can be used other than the garment or support structure 112 shown in FIG. 1.

In the example shown in FIG. 1, the ECG electrodes can be placed circumferentially around the torso of the patient 110 so that the garment or support structure 112 can be used to ensure adequate electrode-skin contact with the patient's skin. It should be noted that other alternative electrode placements may be used, and the scope of the disclosed subject matter is not limited in this respect. For example, adhesive electrode embodiments can provide flexibility in electrode placement in selected locations of the patient's body and may achieve better signal pickup at these selected locations. For example, electrode locations can be selected during a patient-fitting process in which various electrode locations can be changed, and those locations with better or the best ECG signals can be selected, although the scope of the disclosed subject matter is not limited in this respect.

In some embodiments a cardiac monitoring device using the ECG electrodes as shown in FIG. 1 can be configured to detect similar QRS complexes to identify the QRS complexes that are normally conducted through the AV node. Such QRS complexes conducted through the AV node can be referred to herein as "normally conducted QRS complexes". Because the ECG signals can be a mixture of multiple different QRS morphologies, normally conducted QRS complex identification can be used as described herein to more accurately determine the rhythms including but not limited to determining atrial fibrillation (AF) and the associated heart rate (HR) and HR variability, according to one or more embodiments.

According to some embodiments, a cardiac monitoring system or device such as a Wearable Cardioverter Defibrillator (WCD) or a Wearable Cardiac Monitor (WCM) is configured to continuously monitor the patient's ECG signal and generate a rhythm discrimination. In some embodiments the cardiac monitoring device can be configured to detect similar QRS complexes and their P-waves to identify the QRS complexes that are normally conducted through the AV node, referred to herein as normally conducted QRS complexes, and distinguish between different types of SVT. Because the ECG signals can be a mixture of multiple different QRS morphologies and noise, normally conducted QRS complex identification and RR interval and P-wave analysis is used to determine the rhythms more accurately, including classifying SVT rhythms, in accordance with one or more embodiments.

According to some embodiments, a cardiac monitoring device such as a WCD or a WCM can be configured to continuously monitor the patient's ECG signal and detect normally conducted QRS complexes. For arrhythmias with HR in the VT zone, detecting normally conducted QRS complexes can be used to distinguish supraventricular-originated arrhythmias such as AF or SVT from ventricular-originated arrhythmias such as VT or VF. In some embodiments, the normally conducted QRS complexes can be detected by detecting similar QRS complexes. In some embodiments, QRS similarity can be detected by formulating a template of normally conducted QRS complexes and determining a correlation between the formulated template and detected QRS complexes. In other embodiments, QRS similarity can be determined using other approaches, for example comparing the width and amplitude of the QRS complexes. The accuracy of the rhythm analysis can be affected by noise, so analyzing noisy QRS complexes can increase false alarms of the rhythm classification. By analyzing similar QRS complexes as is done in embodiments discussed herein, noise effects can be reduced because noise would tend to make QRS complexes less similar. This in turn tends to increase the accuracy of the rhythm classification and reduce false positives.

Furthermore, normally conducted QRS arrhythmias are not shockable rhythms for a WCD. It is possible that if a conventional WCD mistakenly diagnoses a normally conducted QRS rhythm as a shockable rhythm, it would provide an unnecessary and potentially dangerous shock to the patient.

In addition, as described below, for detected supraventricular-originated arrhythmias, meaning those with normally conducted QRS complexes, the RR interval between consecutive normally conducted QRS complexes and the morphology of their P-waves can be analyzed to classify the rhythm into AF or various SVT rhythms, in some embodiments.

In some embodiments, the cardiac monitoring system can be used in other types of external monitoring devices, for example non-wearable external defibrillators such as those used by emergency medical technicians (EMTs), automated external defibrillators (AEDs), and hospital defibrillators, or in implanted devices. The cardiac monitoring system of such embodiments may be deployed where monitored patients are being transported and causing movement between the ECG sensors and the portion of the patient that the sensors contact or are in high EMI environments, which can introduce noise to the patient's ECG.

Figure 2:
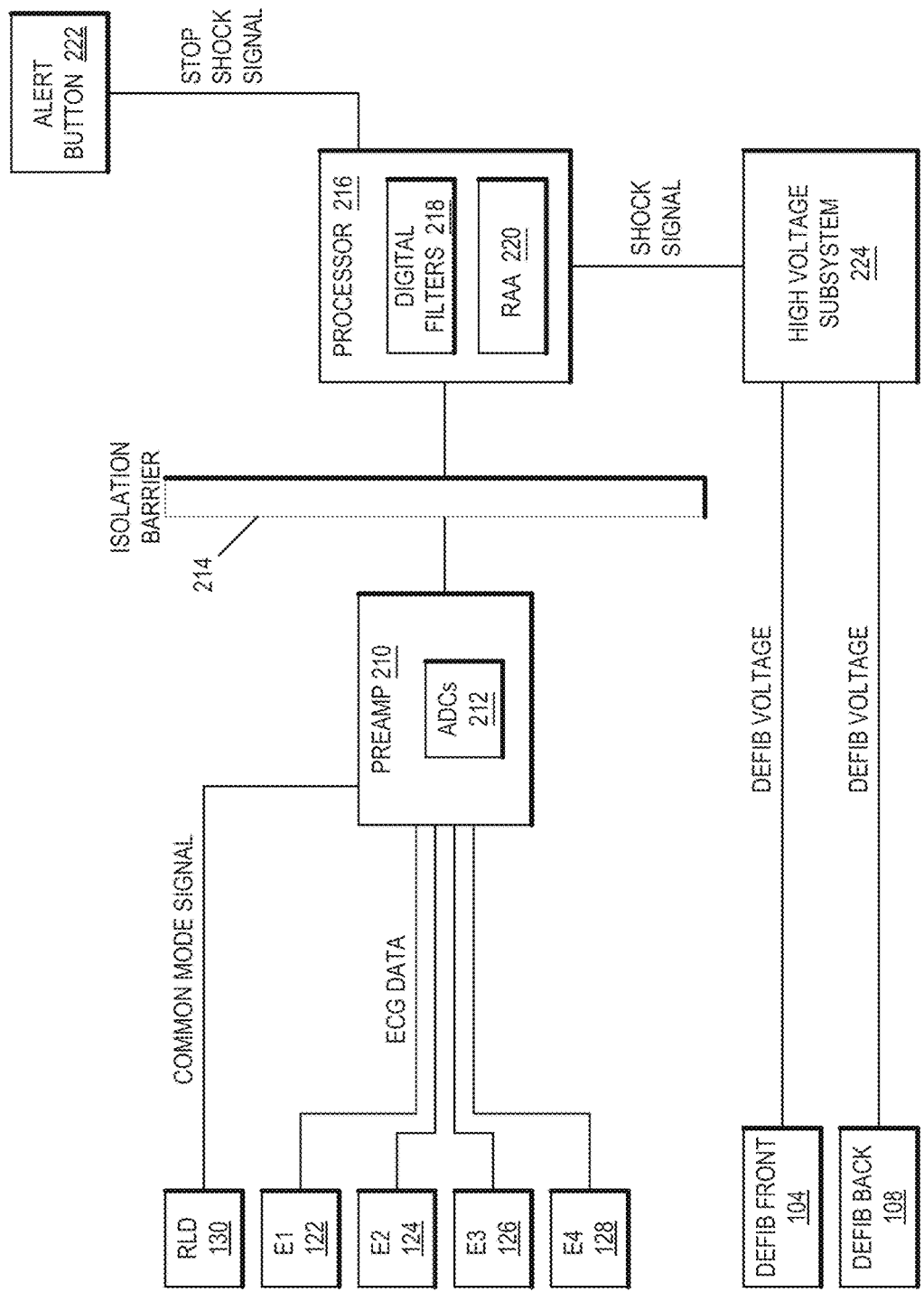
FIG. 2 is diagram of a wearable cardioverter defibrillator (WCD) as an example ECG monitoring device in accordance with one or more embodiments.

Referring now to FIG. 2, a diagram of a wearable cardioverter defibrillator (WCD) as an example ECG or cardiac monitoring device in accordance with one or more embodiments will be discussed. The WCD 200 shown in FIG. 11 incorporates one or more of the features discussed for ECG and QRS complex signal data detection and processing to detect atrial fibrillation (AF) as discussed herein. The ECG electrodes, E1 122, E2 124, E3 126, and E4 128, can comprise silver or silver plated copper electrodes that "dry" attach to the skin of the patient 110. The ECG electrodes provide ECG data to preamplifier 210. The preamplifier 210 may have a wide dynamic range at its input, for example +/−1.1 V which is much larger than the amplitude of the ECG signals which are about 1 mV. The preamplifier 210 can include one or more analog-to-digital converters (ADCs) 212 to convert the ECG signals into a digital format. A right-leg drive (RLD) electrode 130 can be used to provide a common mode signal so that the ECG signal from the ECG electrodes can be provided to preamplifier 210 as differential signals. The digital ECG signals are provided from the preamplifier 210 eventually to a main processor 216 via an isolation barrier 214 which operates to electrically isolate the preamplifier 210 and the ECG signals from the rest of the circuitry of WCD 200. In some examples, the ECG signals are provided to preamp 210 and converted to a digital format using ADCs 212 at which point differential vectors are formed. The differential vectors can then be filtered by digital filters 218 at which point QRS complexes can be detected.

The processor 216 processes the digital ECG data received from the preamplifier 210 with one or more digital filters 218. Since the preamplifier 210 has a wide dynamic range that is much wider than the amplitude range of the ECG signals, digital filters 218 can be utilized to process the ECG data without concern for clipping the incoming signals. One of the digital filters 218 can include a matched filter to facilitate identification of QRS pulses in the incoming data stream. The wide dynamic range of the preamplifier 210 allows at least most of the ECG filtering to happen in software without the signal being clipped. Digital filters 218 can be very effective at removing artifacts from the ECG data. In some examples, digital filters 218 can include one or more bandpass filters to filter the ECG data as discussed in further detail below.

In some examples, the processor 216 can apply a rhythm analysis algorithm (RAA) 220 using QRS width information and heart rate data extracted from the digital ECG data using a segment-based processing analysis and the QRS width versus heart rate analysis to make a shock or no-shock determination. In some embodiments, segment-based processing analysis can be performed as described in US 2019/0030351 A1 "Wearable Cardioverter Defibrillator (WCD) System Reacting to High-Frequency ECG Noise". Said US 2019/0030351 A1 is hereby incorporated herein in its entirety. The RAA 220 receives the digitized ECG signal and calculates the heart rate and QRS width for each segment. The digitized ECG signal is passed over the isolation barrier 214, and the heart rate is derived from the digitized ECG signal. The heart rate and QRS width can be used for making a shock/no-shock decision for each segment, which then can lead to an alarm and a shock. In the event a shockable event is identified, the processor 216 will open a tachycardia episode to start the shock process. Unless the patient 110 provides a patient response using the stop button 222 or other user interface to send a stop shock signal to the processor 216 to intervene before the shock is applied, the processor 216 can send a shock signal to the high voltage subsystem 224 which will apply a defibrillation voltage across the defib front electrode 104 and the defib back electrode 108 to apply one or more therapeutic shocks. In embodiments, the system will provide such shocks until there is no longer any shockable event (VT or VF), or until the energy in a battery or capacitor of high voltage subsystem 224 is depleted or after a predetermined number of shocks have been delivered.

In one or more embodiments of WCD 200, the digital filters 218 coupled with the wide dynamic range of the preamplifier 210 can allow analysis of signals that otherwise would be clipped in systems with a more limited dynamic range. In addition, the matched filter of the digital filters 218 preferentially highlights complexes similar to the patient's normal rhythm. As a result, artifacts that otherwise may be difficult to discriminate using other methods may be significantly attenuated by the matched filter to identify QRS complexes.

It should be noted that a subset of the elements of the WCD 200 of FIG. 2 can be used as a cardiac or ECG monitoring device, or a WCM device, and optionally can be used in conjunction with the support structure 112 of FIG. 1. For example, a cardiac monitoring device can comprise electrodes 122 through 128 (E1-E4) and electrode 130 (RLD), preamp 210, and processor 216, optionally with isolation barrier 214. For a WCM embodiment, the electrodes can be implemented as part of support structure 112. For a WCD embodiment, in addition to the ECG electrodes being in support structure 112, the support structure 112 can also include defibrillation front and back electrodes 104 and 108, and the WCD 200 can include the high voltage subsystem 224 and alert button. 222. Other various elements or subsystems may be used in various other combinations, as a subset or a superset of the elements shown in FIG. 2, as part of a cardiac or ECG monitoring system, WCM, WCD, AED, or the like, to implement the functions of the particular embodiment of the cardiac monitoring system, and the scope of the disclosed subject matter is not limited in these respects.

Figure 3:
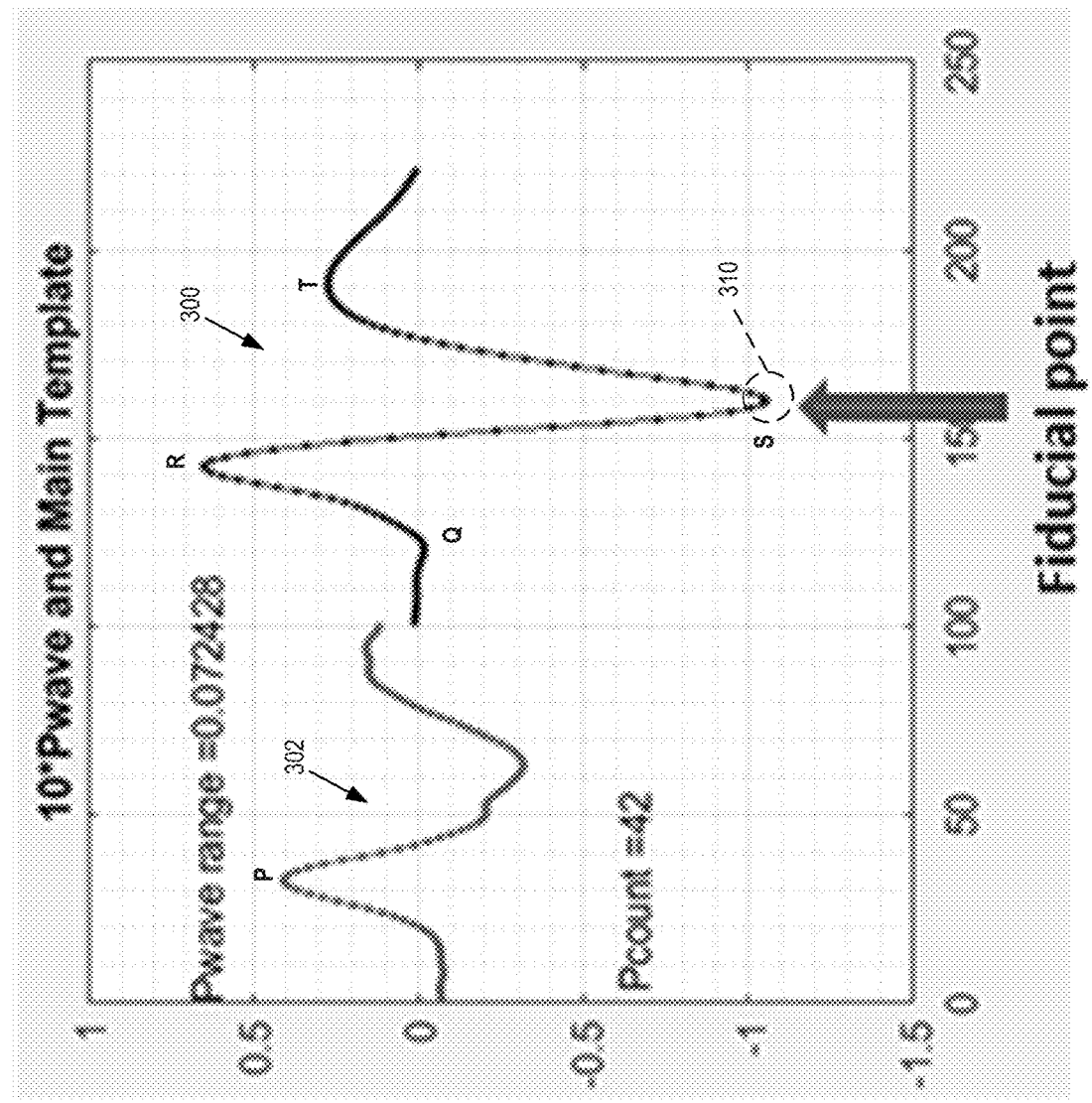
FIG. 3 is a diagram of an identified QRS complex sampled waveform in accordance with one or more embodiments.

Referring now to FIG. 3, a diagram of an identified QRS complex sampled waveform in accordance with one or more embodiments will be discussed. As discussed herein, an ECG monitoring device can be used to monitor ECG signals of a patient 110 and to detect QRS complexes in the ECG signals. The QRS complexes can then be analyzed to detect when the patient is experiencing AF. FIG. 3 shows an example QRS complex 300 waveform plotted in amplitude in millivolts (mV) versus time in milliseconds (ms) on the horizontal axis. The horizontal axis of FIG. 3 can be 2 ms per sample point (500 samples per second) as one example. In the example QRS complex 300 a minimum value is shown at point 310 which corresponds to the S portion of the complex and can be referred to as a fiducial point. It is noted, however, that this is merely an example QRS complex, and the minimum value can be at other points on the plotted QRS complex 300, and the scope of the disclosed subject matter is not limited in this respect. In addition, an example P-wave 302 is shown in the chart. The atrial waveform is multiplied by 10 to make the P-wave 302 more visible in the example shown in FIG. 3, and the T-wave occurs after the QRS complex. Sampled QRS complexes from the patent's ECG signals can be processed and analyzed as part of template based analysis as discussed below.

Figure 4:
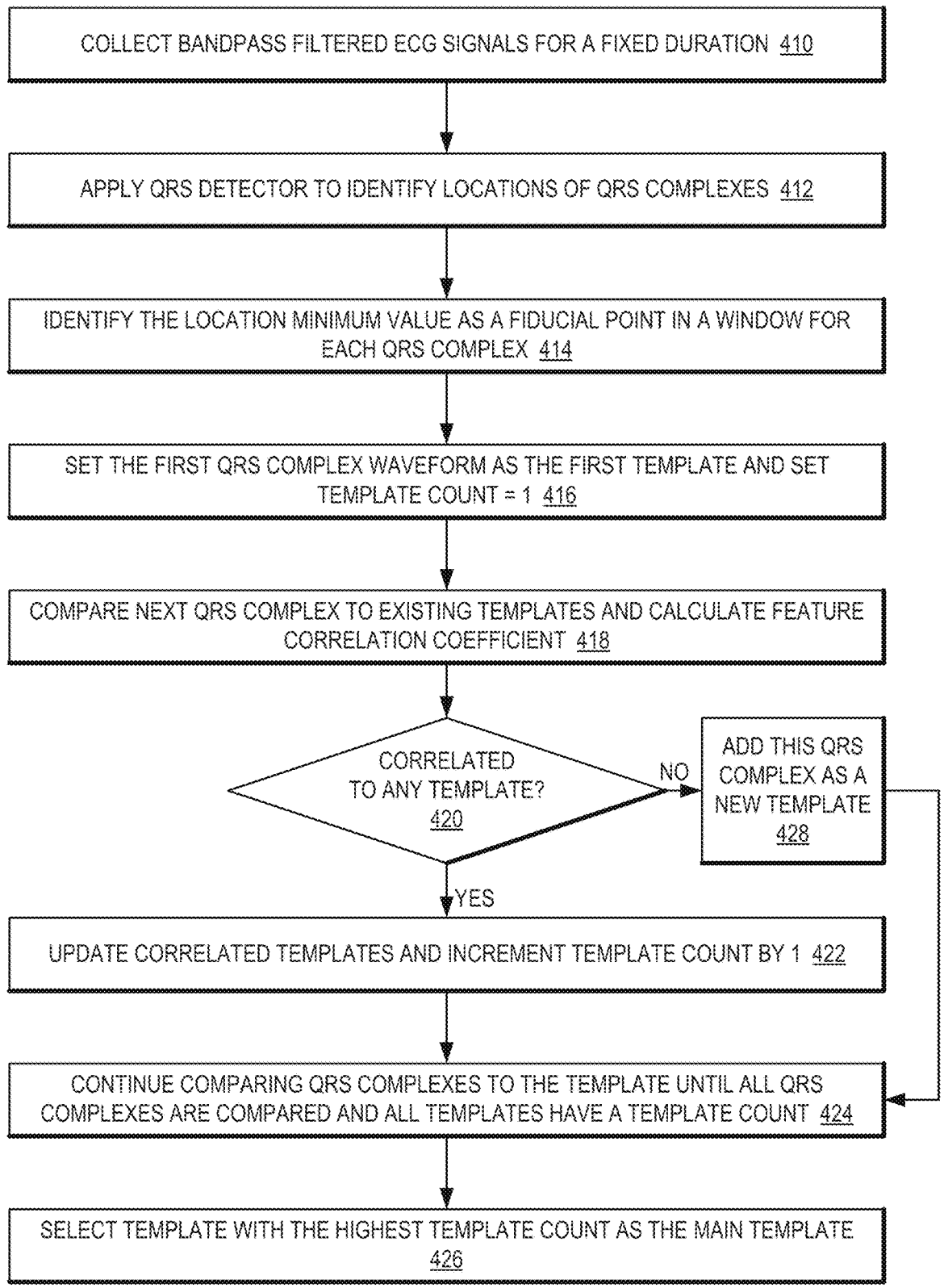
FIG. 4 is a diagram of a method to identify a main template from a series of QRS complexes in accordance with one or more embodiments.

Referring now to FIG. 4, a diagram of a method to identify a main template from a series of QRS complexes in accordance with one or more embodiments will be discussed. Although FIG. 4 shows one implementation of method 400, method 400 can include more or fewer operations than shown and various other orders of the operations than shown, and the scope of the disclosed subject matter is not limited in these respects. The method 400 of FIG. 4 can be implemented as part of template based AF detection. Current American Heart Association (AHA) guidelines define the presence of atrial fibrillation (AF) as electrocardiographic documentation of absolutely irregular RR intervals and no discernible, distinct P waves lasting for at least 30 seconds. There are many ways AF burden can be defined, such as the duration of the longest AF episode, number of AF episodes, or the percentage of time the patient 110 is in AF during a certain monitoring period. Accordingly, an ECG or cardiac monitoring device as discussed herein can measure the RR intervals and RR interval variability of consecutive normally conducted QRS complexes. Furthermore, since AF is not an immediately life-threatening arrhythmia, detecting the onset of AF is generally not critical. Accordingly, an ECG or cardiac monitoring device in accordance with one or more embodiments need not use real-time approaches for AF detection. In some examples, a segment-based approach with relatively long segments, for example over one minute long, can be used. It should be noted that a normal segment length can be about 4 or 5 seconds, and an analyzed segment can range anywhere from about 2 seconds up to about 2 minutes, and the scope of the disclosed subject matter is not limited in this respect.

In some embodiments, the ECG or cardiac monitoring device can comprise a wearable cardioverter defibrillator such as WCD 200 having multiple ECG vectors from multiple electrodes for monitoring the patient 110. In some embodiments, a template of the selected channel can be formulated using method 400, and AF can be detected as described with respect to FIG. 5 below. In some embodiments, the template formulation process can be performed when the patient's HR is detected to be below the VT threshold, for example 110 beats per minute (bpm). The entire process can be applied after template formulation for rhythm classification, for any HR. In some embodiments, some operations can be performed using the existing template formed at a slower rate when the patient's HR is detected to exceed the VT threshold. For example, a VT threshold can be set to 170 bpm in a WCD embodiment).

At operation 410, bandpass filtered ECG signals can be collected for a fixed duration. As an example, the bandpass filter may have a bandwidth of about 8 Hz to about 25 Hz, and the fixed duration can be 60 seconds. At operation 412, a QRS detector can be applied to the filtered ECG signal to identify locations of QRS complexes in the ECG signal. Any suitable QRS detector can be used, for example, a QRS detector as disclosed in published US patent application US 2018/0093102 A1 titled WEARABLE CARDIOVERTER DEFIBRILLATOR (WCD) WITH POWER-SAVING FUNCTION. Said published application US 2018/0093102 A1 is hereby incorporated herein in its entirety. At operation 414, for each QRS complex the location of the minimum value can be identified as the fiducial point in a window, for example 160 ms starting from the detection point. For example, the minimum value can be the minimum value 310 shown in FIG. 3, and the waveform window can start 120 ms before the fiducial point and have a duration of 240 ms.

At operation 416, the first QRS complex waveform can be set as the first template, and the template count can be set to a value of one (template count=1). In some examples, if there is an existing template, the existing template optionally can be the starting template with a template count of one. At operation 418, the next QRS complex waveform can be compared to the existing template waveform. The concept is to identify similar QRS complexes. If the next QRS complex does not match or is not correlated with the existing template or any template as determined at decision block 420, then the method continues by comparing the next QRS complex to the template. If the current QRS complex is not correlated to any templates, then this QRS complex can be used as a new template by adding this QRS complex as a new template at operation 428. The size or number of the templates can increase as more uncorrelated QRS complexes are detected. If the next QRS complex waveform is correlated with the existing template as determined at decision block 420, the existing template can be updated at block 422, and the template count can be incremented by one. The current QRS complex can be correlated to multiple templates, and the count of each of the templates can increase by one for each match. Optionally, in some embodiments, a comparison can be made with the fiducial points 310 to determine fiducial point shift, for example a minimum point −2 to minimum point +2. The fiducial point with the best match can be selected. In some examples, the correlation decision can be made based on calculation of a feature correlation coefficient (FCC). In other examples, other measures of correlation can be used, for example a sample correlation coefficient (SCC) wherein FCC is a squared version of SCC and the scope of the disclosed subject matter is not limited in this respect. Other measures of correlation or similarity can be utilized, for example comparison of the height and/or or width of the QRS complexes to the template, a normalized area difference method which measures the area difference between the QRS complex and the template divided by the area of the template, a frequency domain analysis method, and so on. As an example, for one dataset {x1, . . . , xn} containing n values and another dataset {y1, . . . , yn} containing n values, then that formula for sample correlation coefficient (SCC) r is:

$$r = r_{xy} = \frac{\sum_{i=1}^{n}(x_i - \bar{x})(y_i - \bar{y})}{\sqrt{\sum_{i=1}^{n}(x_i - \bar{x})^2}\sqrt{\sum_{i=1}^{n}(y_i - \bar{y})^2}}$$

In the equation above, the x data values can correspond to the values of a sampled QRS complex waveform being compared to the template, and the y data values can correspond to the template to which a the QRS complex waveform is being compared, wherein $\bar{x}$ and $\bar{y}$ are the average x and y values in each dataset. The SCC has value between −1 and 1 wherein for perfect match the SCC value will be 1. In some examples, if SCC>0.9, then the QRS complex can be considered as correlated with the template, and the existing template is updated by:

Updated template=0.9*current template+0.1*current QRS complex

In the above equation, to arrive at the values of the updated template, the values in the current template are each multiplied by 0.9 and the values of the current QRS complex are multiplied by 0.1, then the corresponding values are added to arrive at the values for the updated template. It should be noted that although weighting multipliers 0.9 and 0.1 in the above example can be used for some embodiments, other values of multipliers can be used in other embodiments, for example 0.8 and 0.2 or 0.95 and 0.005, and so on, and the scope of the disclosed subject matter is not limited in this respect. At operation 424, QRS complexes can continue to be compared to the existing template until all QRS complexes have been compared and all templates have a template count value. The template having the highest template count, meaning the most similarity to the greatest number of the QRS complexes in a given segment of QRS complexes, can be selected at operation 426 to be the main template. If the highest template count is more than 50 percent of the number of detected QRS complexes in the segment, then the main template is selected as the main template of this segment. Otherwise, the segment can be considered to be an unstable situation and therefore the segment can be skipped. The main template can then be used to identify normally conducted QRS complexes to detect AF using RR intervals in the normally conducted QRS complexes according to FIG. 6 below. An example of an RR interval is shown in and described with respect to FIG. 5 below.

Figure 5:
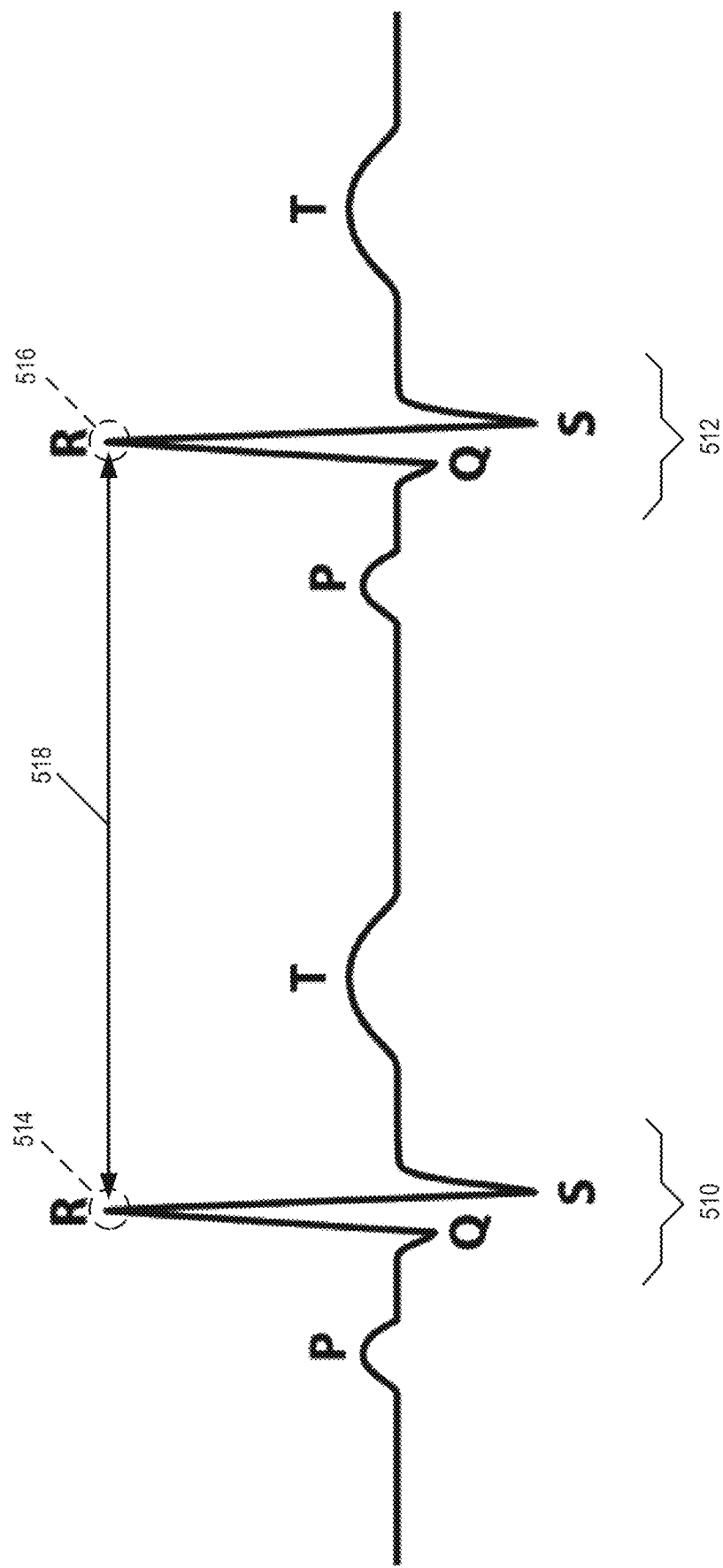
FIG. 5 is a diagram illustrating RR intervals between QRS complexes in accordance with one or more embodiments.

Referring now FIG. 5, a diagram illustrating RR intervals between QRS complexes in accordance with one or more embodiments will be discussed. After the main template has been identified as determined according to method 400 of FIG. 4 above, the main template can be used to determine RR intervals between consecutive normally conducted QRS complexes to determine whether the patient 110 is experience atrial fibrillation (AF). FIG. 5 shows an example of an RR interval between two successive QRS complexes, QRS complex 510 and QRS complex 512. The RR interval 518 between these two QRS complexes is the time between the R peaks of each of the QRS complexes. It should be noted that although the minimum point in the QRS complex can be used as the fiducial point 310, since the polarity is determined by the way differential vectors are formed, other fiducial points can be used other than the minimum point. The RR interval 518 between multiple consecutive QRS complexes can be determined as discussed with respect to FIG. 6, below.

Figure 6:
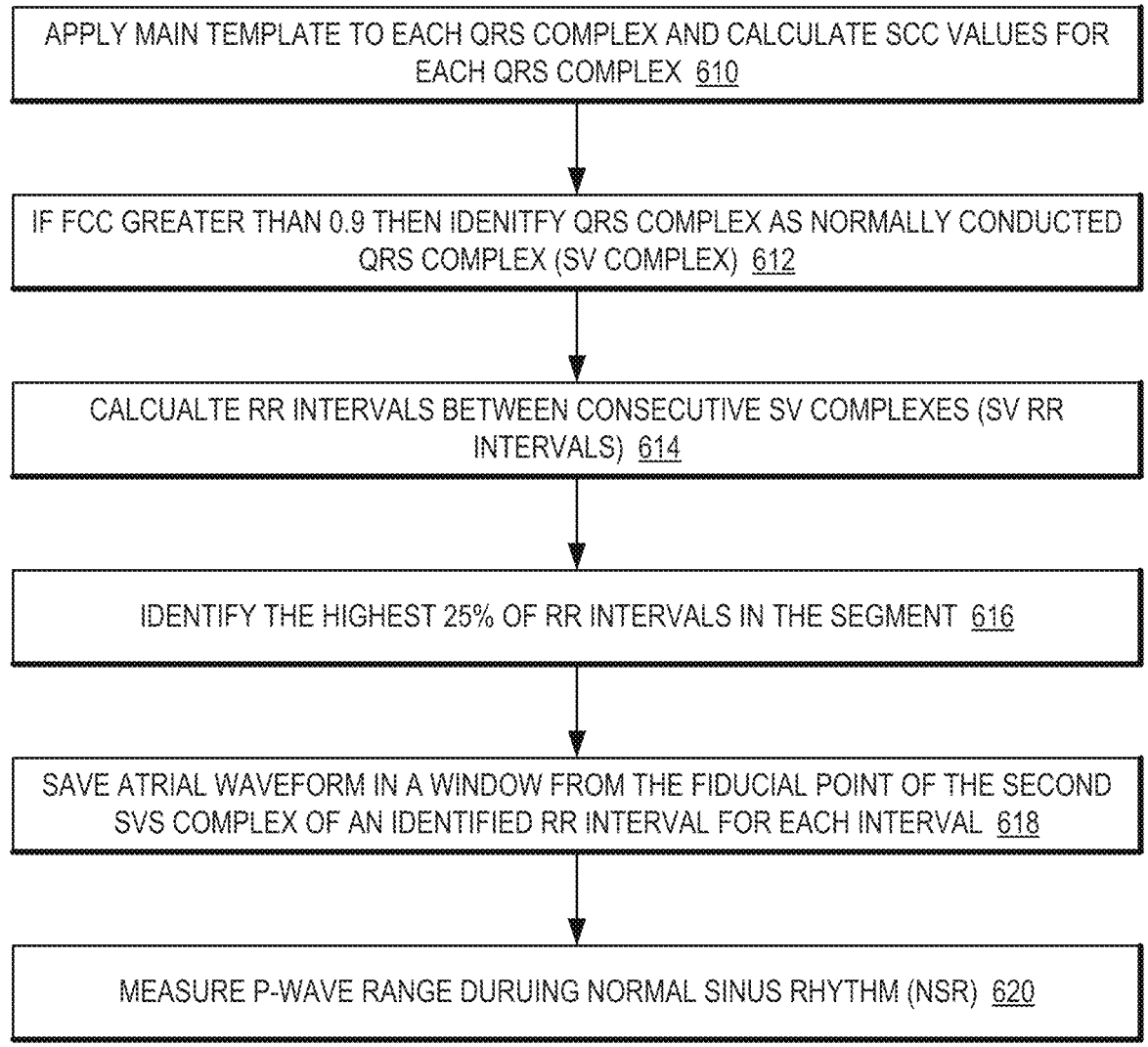
FIG. 6 is a diagram of a method to identify RR intervals between similar QRS complexes in accordance with one or more embodiments.

Referring now to FIG. 6, a diagram of a method to identify RR intervals between similar QRS complexes in accordance with one or more embodiments will be discussed. Although FIG. 6 shows one implementation of method 600, method 600 can include more or fewer operations than shown and various other orders of the operations than shown, and the scope of the disclosed subject matter is not limited in these respects. Method 600 can be performed after the main template is identified according to method 400 of FIG. 4. In some embodiments, after a template of the selected channel is formulated, normally conducted QRS complexes can be identified, and the rhythm can be classified as described below to distinguish between AF and various SVT rhythms. In some embodiments, the template formulation process can be performed as described in U.S. Provisional Application No. 62/890,313 filed Aug. 22, 2019 "Cardiac Monitoring System with Normally Conducted QRS Complex Identification". Although only one channel is described for illustration, in some examples multiple channels can be used. In some embodiments, four channels can be used out of six possible differential channels formed from four independent electrodes placed around the chest of a patient 110. In other embodiments, a different number of channels, including only one channel, can be used. In WCM embodiments, a different number of electrodes can be used, often a reduced number of electrodes, or a different garment system can be used compared to the garment or support structure 112 shown in FIG. 1.

At operation 610, the main template can be applied to each QRS complex in a given segment of QRS complexes. The FCC values of each of the QRS complexes can then be calculated, or alternatively SCC values can be calculated in some embodiments. At operation 612, if the FCC value (or SCC value) for a QRS complex is greater than 0.9 or some threshold, then that QRS complex can be considered as a normally conducted QRS complex, and can be labeled as a supraventricular (SV) complex, meaning that the QRS complex is a normally conducted QRS complex that originate above the sinoatrial (SA) node. It should be noted that although an FCC value (or an SCC value) of 0.9 can be used as a matching or correlation threshold as an example, other values for the FCC or SCC can be used as a threshold, and the scope of the disclosed subject matter is not limited in this respect. For example, an FCC range of 0.8 to 0.9 can be used, and an SCC range of 0.9 to 0.95 can be used. At operation 614, the RR intervals 518 between consecutive SV complexes can be calculated, and the RR intervals can be labeled as SV RR intervals. It should be noted that QRS complexes having FCC values (or SCC) values below the threshold, such as having value below 0.9, are disregarded since such uncorrelated QRS complexes can be considered as not being normally conducted QRS complexes or otherwise are noisy.

At operation 616, the highest 25 percent of RR intervals in the ECG segment can be identified. In some embodiments, this threshold can range from about 20 percent to about 30 percent, and the scope of the disclosed subject matter is not limited in this respect. At operation 618, for each identified RR interval, the atrial waveform can be saved in a window between 260 ms and 120 ms from the fiducial point of the second SV complex of an RR interval. In some embodiments, the window can be defined to have a range large enough to capture the P-waves along with the QRS complexes. At operation 620, the P-wave range can be measured during normal sinus rhythm (NSR) and saved as described above to be used later for SVT rhythm classification.

Figure 7:
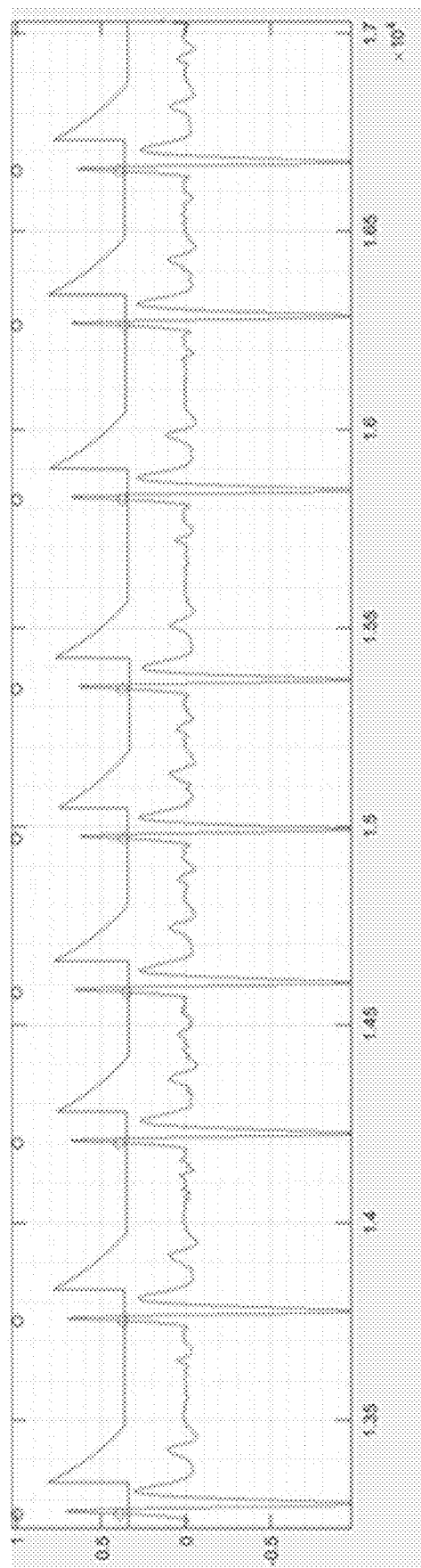
FIG. 7 is a diagram of an ECG signal showing distinctive depolarization waveforms in accordance with one or more embodiments.
Figure 8:
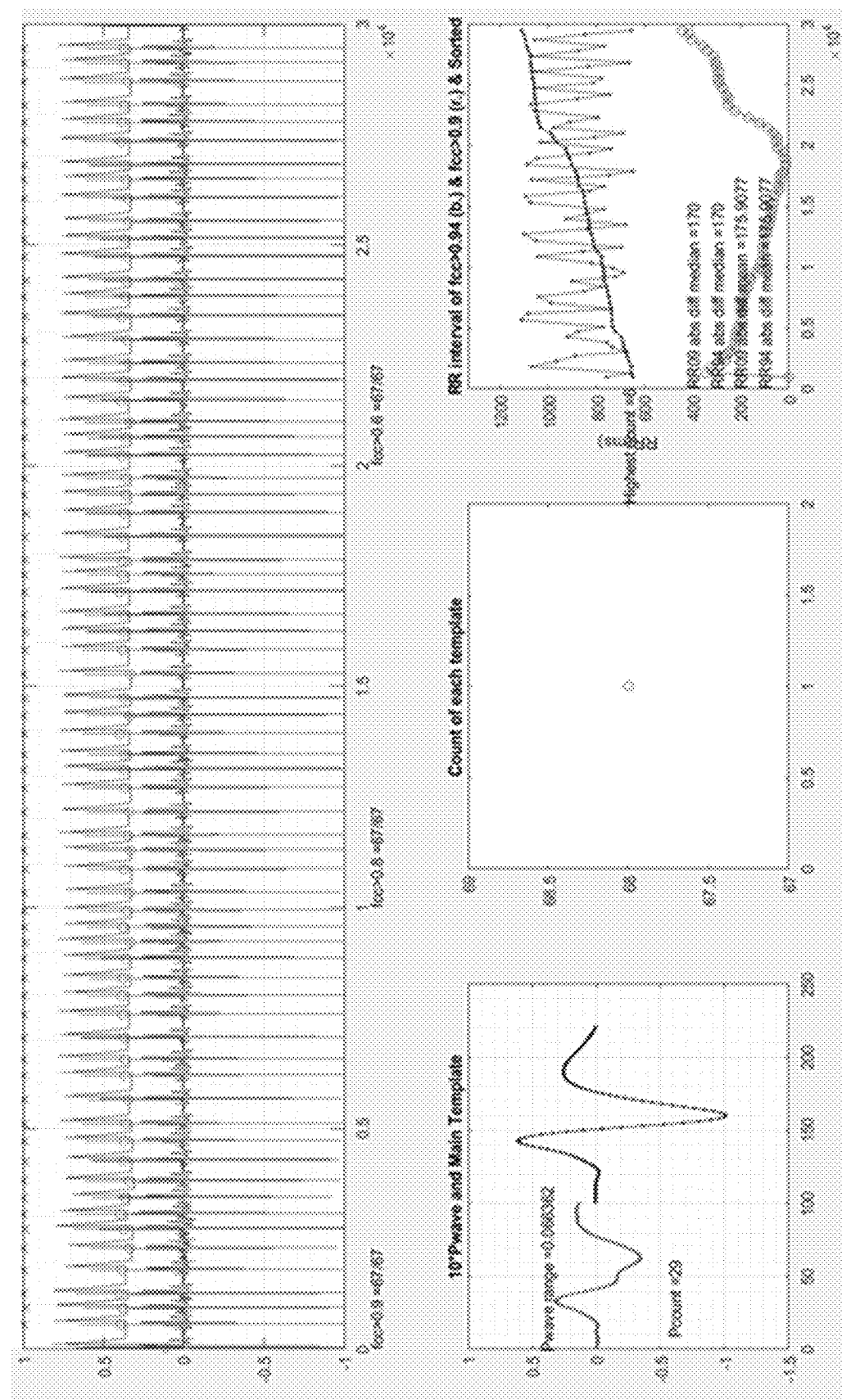
FIG. 8 is a diagram of the ECG signal of FIG. 7 showing a different scale including the HR variability of the ECG signal in accordance with one or more embodiments.

Referring now to FIG. 7 and FIG. 8, a diagram of an ECG signal at different scales and the HR variability of the ECG signal in accordance with one or more embodiments will be discussed. Current American Heart Association (AHA) guidelines define the presence of atrial fibrillation (AF) as electrocardiographic documentation of absolutely irregular RR intervals and no discernible, distinct P waves lasting for at least 30 seconds. In some embodiments, the RR intervals and RR interval variability of consecutive normally conducted QRS complexes can be measured. Furthermore, since AF and some other supraventricular tachycardia (SVT) rhythms are not an immediately life-threatening arrhythmia, detecting the onset of AF or such SVT rhythms is generally not critical. Accordingly, real time approaches for classifying these rhythms are not used in some embodiments. For example, a segment-based approach with relatively long segments, for example over one minute long, can be used.

High heart rate (HR) variability has been observed in AF and in other SVT rhythms, so HR variability alone is not used to classify the rhythm in some embodiments. For example, the rhythm shown in FIG. 7 has a distinctive atrial depolarization waveforms, which indicates the rhythm is not AF. The same rhythm is shown in FIG. 8 using a different scale. The HR variability is shown right bottom chart which shows a high HR variability which is similar to AF. In accordance with some embodiments, identify normally conducted QRS complexes can be identified and combined with P-wave analysis to classify rhythms into AF and other SVT rhythms with enhanced accuracy.

Figure 9:
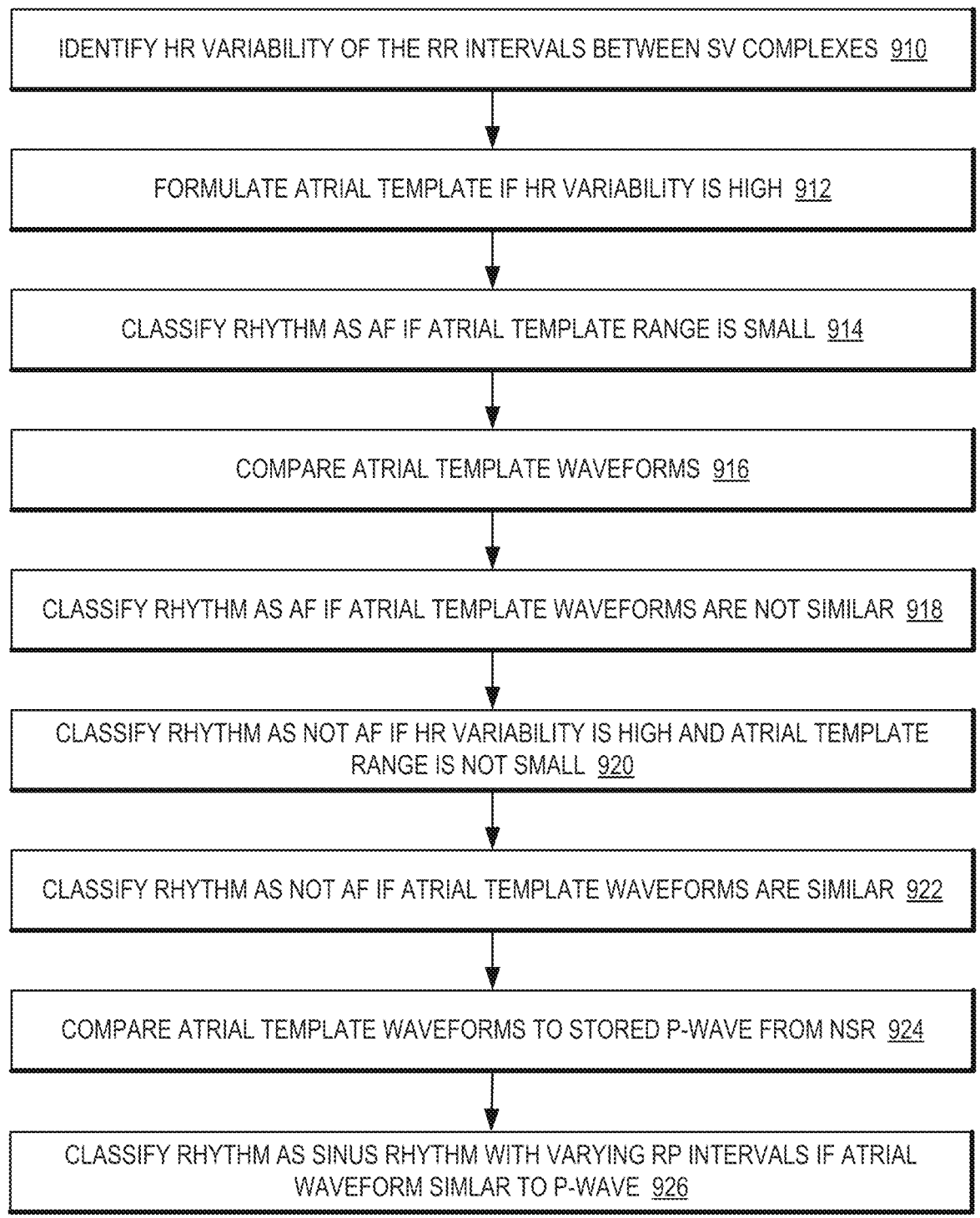
FIG. 9 is a diagram of a method for SVT rhythm classification in accordance with one or more embodiments.

Referring now to FIG. 9, a diagram of a method for SVT rhythm classification in accordance with one or more embodiments will be discussed. Although FIG. 9 shows one implementation of method 900, method 900 can include more or fewer operations than shown and various other orders of the operations than shown, and the scope of the disclosed subject matter is not limited in these respects. At operation 910, the variability of the RR intervals can be referred to as HR variability such that the HR variability can be identified from the RR intervals between the SV complexes.

In some embodiments, at operation 912 an atrial template can be formulated for example using the template formation method 400 of FIG. 4. If the atrial template range is small, then the rhythm can be classified as AF at operation 914 in one or more embodiments. An example of a P-wave template is shown in and described with respect to FIG. 11, below. At operation 916, to further enhance specificity the atrial template waveforms can be compared. If the atrial template waveforms are not similar, then the rhythm can be classified as AF at operation 918. After formulating the atrial templates, if the HR variability is high and the atrial template range is not small, then the rhythm can be classified as not AF at operation 920 in some embodiments. Another example of P-wave templates is shown in and described with respect to FIG. 12 below.

At operation 922, if the atrial template waveforms are similar, then the rhythm can be classified as not AF. In some embodiments, this rhythm can be an SVT rhythm such as premature atrial contraction (PAC). In other embodiments, the atrial waveforms can be compared to a stored P-wave from a normal sinus rhythm (NSR) at operation 924. If the atrial waveform is similar to the P-wave, then the rhythm can be classified as a sinus rhythm with varying RP intervals at operation 926.

Figure 10:
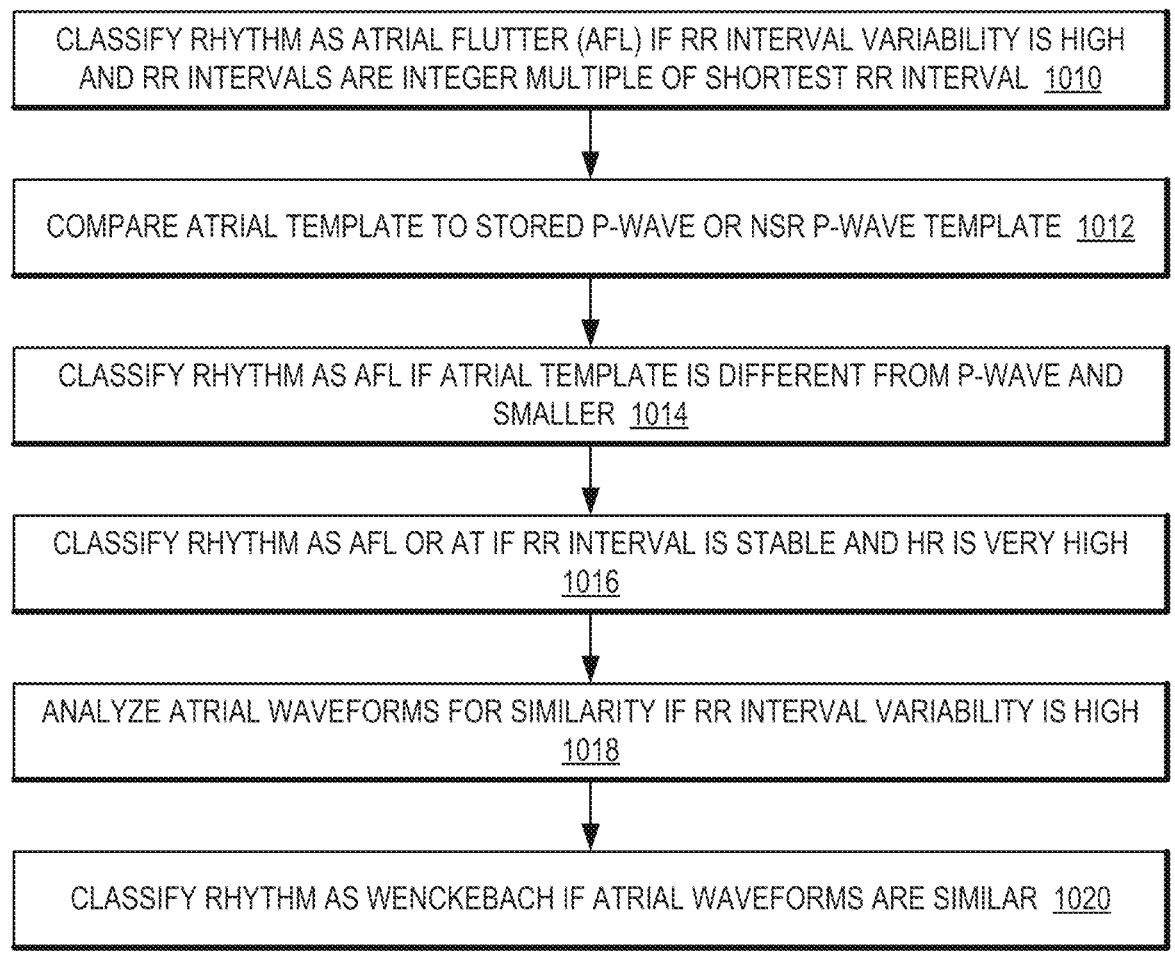
FIG. 10 is a diagram of an additional method for SVT rhythm classification in accordance with one or more embodiments.

Referring now to FIG. 10, a diagram of an additional method for SVT rhythm classification in accordance with one or more embodiments will be discussed. Although FIG. 10 shows one implementation of method 1000, method 1000 can include more or fewer operations than shown and various other orders of the operations than shown, and the scope of the disclosed subject matter is not limited in these respects. At operation 1010, if RR interval variability high and the RR intervals are integer multiple of the shortest RR interval, then the rhythm can be classified as atrial flutter (AFL). At operation 1012, in some embodiments, the atrial template can be compared to a stored P-wave or P-wave template taken during NSR. At operation 1014, if the atrial template is different from the P-wave and smaller, then the rhythm can be classified as AFL in some embodiments. At operation 1016, if the RR interval is stable and the HR is very high, for example higher than 180 bpm, then the rhythm can be classified as AFL or atrial tachycardia (AT) AF as a further refinement in some embodiments. In some embodiments, if RR interval variability is high, at operation 1018 atrial waveforms can be analyzed for similarity for example when the RR intervals are all within the 10% of the median RR interval. At operation 1020, if the atrial waveforms are similar then the rhythm can be classified as Wenckebach in some embodiments. It should be noted that other SVT rhythm can be detected using HR, HR variability, RR interval patterns, or atrial template compared to P-wave template, and the scope of the disclosed subject matter is not limited in this respect. In some embodiments, the methods described herein can implemented by cardioverter defibrillator, for example as shown in and described with respect to FIG. 2. In such embodiments, the cardioverter defibrillator can comprise a housing to contain a processor, a memory, and a high voltage subsystem, and optionally other components shown for example in FIG. 2. In some embodiments, the housing can be affixable to a body or skin of the patient via an adhesive. In other embodiments, the housing can be implantable in a subcutaneous location of a body of the patient. It should be noted that these embodiments are some examples of a cardiac monitoring system or a cardioverter defibrillator, and the scope of the disclosed subject matter is not limited in these respects.

Figure 11:
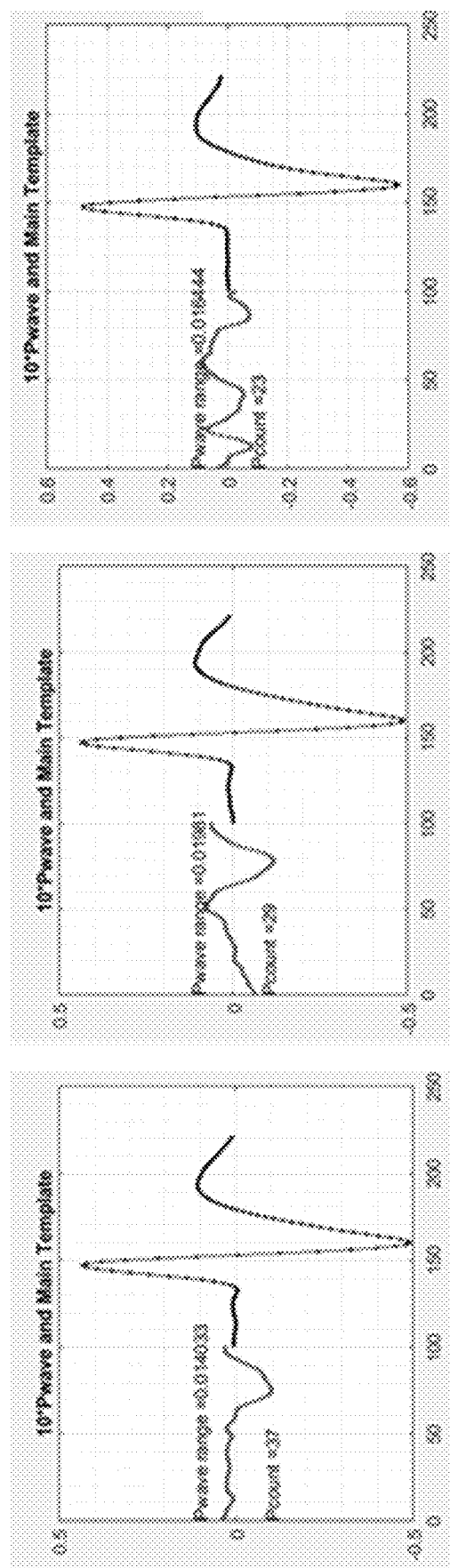
FIG. 11 is a diagram of example atrial templates including P-wave templates in accordance with one or more embodiments.

Referring now to FIG. 11, a diagram of example atrial templates including P-wave templates in accordance with one or more embodiments will be discussed. Three examples from the same patient are shown in FIG. 11 with 10× magnification of the P-wave templates. The P-wave templates of each of the examples show a relatively small the P-wave range and varying morphology. If the P-wave template of the received QRS complex window is less than a threshold percentage, for example 25% in some embodiments, of the stored P-wave range measured during normal sinus rhythm (NSR) and shown in the windows shown in the charts of FIG. 11, then the rhythm can be classified as AF.

Figure 12:
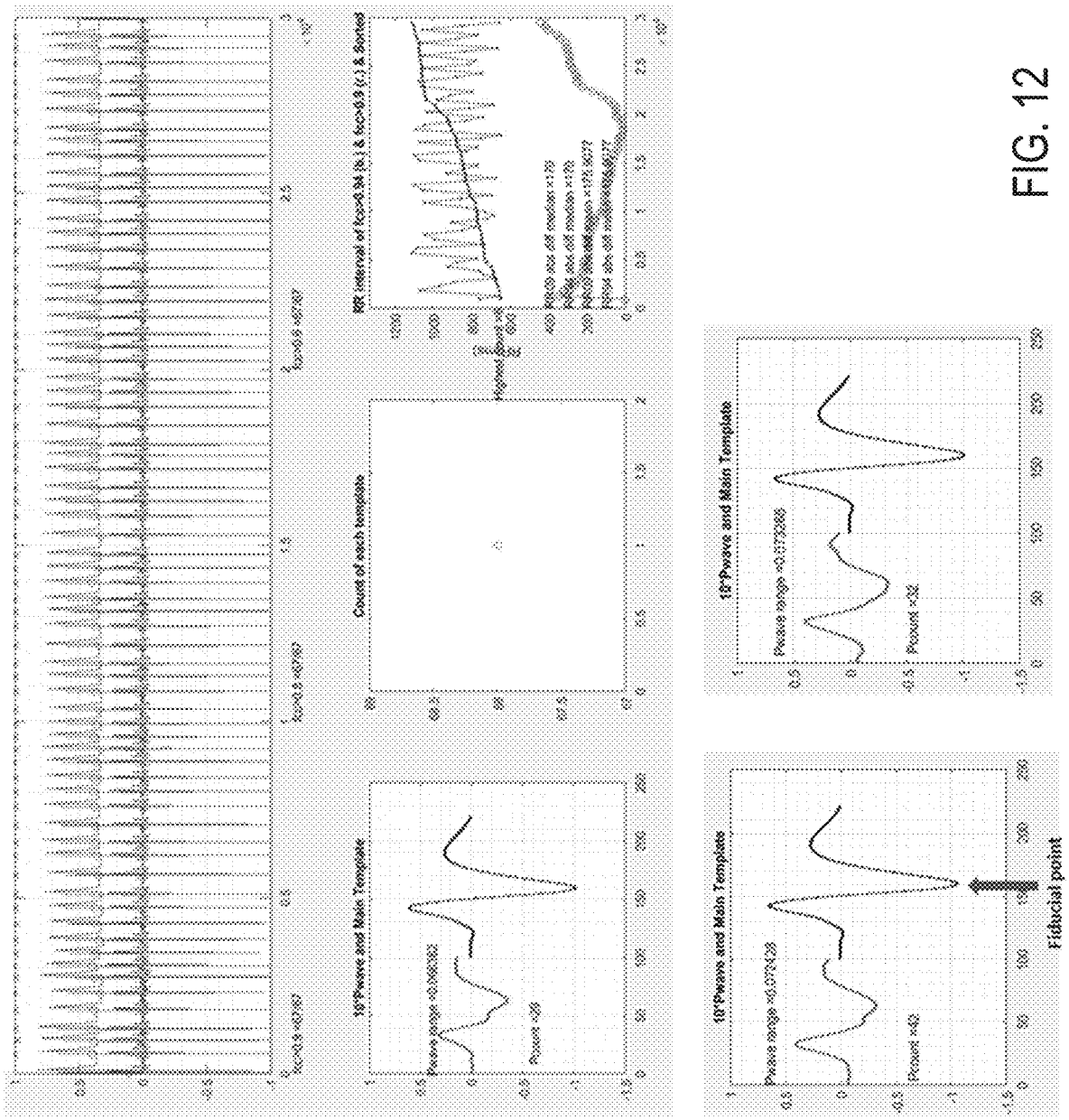
FIG. 12 is a diagram of additional examples of atrial templates including P-wave templates in accordance with one or more embodiments.

FIG. 12 is a diagram of additional examples of atrial templates including P-wave templates in accordance with one or more embodiments. The charts of FIG. 12 show another example of three measurements from the same patient, but a different from the patient of FIG. 11. FIG. 12 shows a similar amplitude of P-wave templates, for example larger than 50% of the P-wave range measured from NSR as previously described, and the consistent morphology. In one or more embodiments, these rhythms are classified as not AF.

Although the claimed subject matter has been described with a certain degree of particularity, it should be recognized that elements thereof may be altered by persons skilled in the art without departing from the spirit and/or scope of claimed subject matter. It is believed that the subject matter pertaining to a cardiac monitoring system with supraventricular tachycardia (SVT) classifications and many of its attendant utilities will be understood by the forgoing description, and it will be apparent that various changes may be made in the form, construction and/or arrangement of the components thereof without departing from the scope and/or spirit of the claimed subject matter or without sacrificing all of its material advantages, the form herein before described being merely an explanatory embodiment thereof, and/or further without providing substantial change thereto. It is the intention of the claims to encompass and/or include such changes.

What is claimed is:

1. A cardiac monitoring system, comprising:
a processor configured to receive a segment of an electrocardiogram (ECG) signal of a patient;
a memory to store the segment of the ECG;
wherein the processor is configured to:
    identify normal sinus rhythm (NSR) complexes in the segment of the ECG signal as SV complexes;
    measure RR intervals between consecutive pairs of the SV complexes;
    determine RR variability from the measured RR intervals between consecutive pairs of the SV complexes;
    obtain a P-wave waveform from a window of the corresponding SV complex for each of the RR intervals;
    obtain a P-wave template from the P-wave waveforms in the SV complexes;
    measure a range of the P-wave waveforms from the SV complexes;
    save the measured range of P-waves, the P-wave waveforms, and the P-wave template in the memory; and
    classify the identified SV complexes as either atrial fibrillation (AF) or supraventricular tachycardia (SVT) based at least on part the P-wave template and the RR variability;
    wherein the identified SV complexes are classified as AF when the RR variability is greater than a threshold value and an amplitude of the P-wave template is below a predetermined percentage of the P-wave range measured during NSR; and
    wherein the identified SV complexes are classified as SVT when the RR variability is higher than the threshold value and the amplitude of the P-wave template is above the predetermined percentage of the P-wave range; and
a support structure comprising a plurality of ECG electrodes configured to couple to a body of the patient through which the ECG signal of the patient is obtained;
wherein the support structure comprises a plurality of defibrillation electrodes configured to couple to the body of the patient, and a high voltage subsystem to apply a defibrillation voltage to the patient when a shockable event is detected by the processor based at least in part on the classification of the identified SV complexes.

2. The cardiac monitoring system of claim 1, wherein:
the identified SV complexes are classified as atrial flutter (AFL) when the RR variability is high, and the RR intervals are integer multiples of a shortest one of the RR intervals.

3. The cardiac monitoring system of claim 1, wherein the processor is further configured to:
analyze the P-wave waveforms for similarity when the RR variability is high; and
wherein the identified SV complexes are classified as Wenckebach when the P-wave waveforms are similar.

4. A cardioverter defibrillator, comprising:
a housing;
a processor in the housing configured to receive a segment of an electrocardiogram (ECG) signal of a patient;
a memory in the housing to store the segment of the ECG; and
a high voltage subsystem in the housing to apply a defibrillation voltage to the patient;
wherein the processor is configured to:
    identify normal sinus rhythm (NSR) complexes in the segment of the ECG signal as SV complexes;
    measure RR intervals between consecutive pairs of the SV complexes;
    determine RR variability from the measured RR intervals between consecutive pairs of the SV complexes;
    obtain a P-wave waveform from a window of the corresponding SV complex for each of the RR intervals;
    obtain a P-wave template from the P-wave waveforms in the SV complexes;
    measure a range of the P-wave waveforms from the SV complexes;
    save the measured range of P-waves, the P-wave waveforms, and the P-wave template in the memory;
    classify the identified SV complexes as either atrial fibrillation (AF) or supraventricular tachycardia (SVT) based at least on part the P-wave template and the RR variability;
    wherein the identified SV complexes are classified as AF when the RR variability is greater than a threshold value and an amplitude of the P-wave template is below a predetermined percentage of the P-wave range measured during NSR; and
    wherein the identified SV complexes are classified as SVT when the RR variability is higher than the threshold value and the amplitude of the P-wave template is above the predetermined percentage of the P-wave range; and
    apply the defibrillation voltage to the patient when a shockable event is detected based at least in part on the classification of the identified SV complexes.

5. The cardioverter defibrillator of claim 4, wherein the housing includes an adhesive and is affixable to a body of the patient via the adhesive.

6. The cardioverter defibrillator of claim 4, wherein the housing is implantable in a subcutaneous location of a body of the patient.

* * * * *